US00RE38668E

(19) United States
(12) Reissued Patent
Edwards

(10) Patent Number: US RE38,668 E
(45) Date of Reissued Patent: Dec. 7, 2004

(54) METHOD FOR INFERRING METAL STATES FROM EYE MOVEMENTS

(75) Inventor: Gregory T. Edwards, Roseville, CA (US)

(73) Assignee: The Board of Trustees of the Leland Stanford Junior University, Palo Alto, CA (US)

(21) Appl. No.: 10/219,708

(22) Filed: Aug. 14, 2002

Related U.S. Patent Documents

Reissue of:
(64) Patent No.: 6,102,870
Issued: Aug. 15, 2000
Appl. No.: 09/304,542
Filed: May 3, 1999

U.S. Applications:
(63) Continuation of application No. 09/173,849, filed on Oct. 16, 1998, now abandoned.
(60) Provisional application No. 60/062,178, filed on Oct. 16, 1997.

(51) Int. Cl.[7] ..... A61B 13/00
(52) U.S. Cl. ..... 600/558
(58) Field of Search ..... 600/544, 545, 600/558; 128/925, 898; 340/575; 434/258, 259; 351/209, 210, 237, 238, 239, 243, 202, 203

(56) References Cited

U.S. PATENT DOCUMENTS 3,691,652 A * 9/1972 Clynes ..... 434/236
5,280,793 A * 1/1994 Rosenfeld ..... 600/544
5,564,433 A * 10/1996 Thornton ..... 600/544
5,704,369 A * 1/1998 Scinto et al. ..... 600/558
5,724,987 A * 3/1998 Gevins et al. ..... 600/544

OTHER PUBLICATIONS

Jacob, R., Eye tracking in advanced interface design, Human–Computer Interaction Lab, NavalResearch Lab, Washington, D.C, www.eecs.tufts.edu/~jacob/papers/barfield.html.*
Starker, I. et al., A gaze–responsive self–disclosing display, CHI '90 Proceedings, Media Lab, Massachusetts Institute of Technology, Apr. 1990.*
Takagi, H., Development of Predictive Chi with eye Movements, Master Thesis, University of Tokyo, Feb. 7, 1996.*

* cited by examiner

*Primary Examiner*—George Manuel
(74) *Attorney, Agent, or Firm*—Blakely Sokoloff Taylor & Zafman LLP

(57) ABSTRACT

A computer-implemented method infers mental states of a person from eye movements of the person. The method includes identifying elementary features of eye tracker data, such as fixations and saccades, and recognizing from the elementary features a plurality of eye-movement patterns. Each eye-movement pattern is recognized by comparing the elementary features with a predetermined eye-movement pattern template. A given eye-movement pattern is recognized if the elementary features satisfy a set of criteria associated with the template for that eye-movement pattern. The method further includes the step of recognizing from the eye-movement patterns a plurality of eye-behavior patterns corresponding to the mental states of the person. Because high level mental states of the user are determined in real time, the method provides the basis for reliably determining when a user intends to select a target.

39 Claims, 3 Drawing Sheets

FIG. 2A
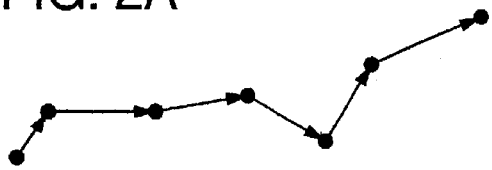
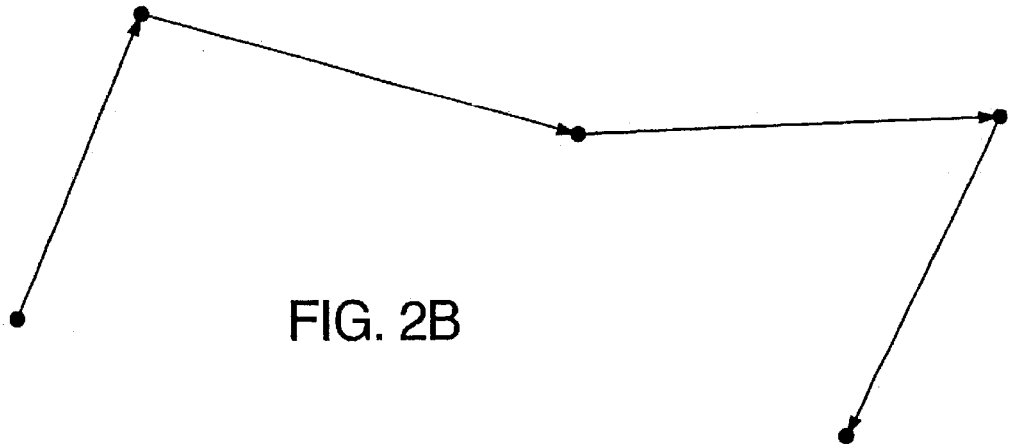
FIG. 2B
FIG. 2C
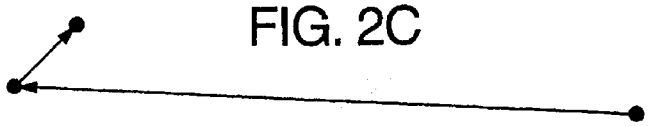

METHOD FOR INFERRING METAL STATES FROM EYE MOVEMENTS

Matter enclosed in heavy brackets [ ] appears in the original patent but forms no part of this reissue specification; matter printed in italics indicates the additions made by reissue.

CROSS-REFERENCE TO RELATED APPLICATIONS

This application is a continuation of U.S. patent application Ser. No. 09/173,849 filed Oct. 16, 1998, *now abandoned,* which claims priority from U.S. provisional patent application Ser. No. 60/062,178 filed Oct. 16, 1997, which is hereby incorporated by reference.

FIELD OF THE INVENTION

The present invention relates generally to the field of eye tracking and methods for processing eye tracking data. In particular, the invention relates to a system and method for determining mental states or mental activities of a person from spatio-temporal eye-tracking data, independent of a priori knowledge of the objects in the person's visual field.

BACKGROUND

In recent years, eye-tracking devices have made it possible for machines to automatically observe and record detailed eye movements. One common type of eye tracker, for example, uses an infrared light-source, a camera, and a data processor to measure eye gaze positions, i.e., positions in the visual field at which the eye gaze is directed. The tracker generates a continuous stream of spatiotemporal data representative of eye gaze positions at sequential moments in time. Analysis of this raw data typically reveals a series of eye fixations separated by sudden jumps between fixations, called saccades.

An informative survey of the current state of the art in the eyetracking field is given in Jacob, R. J. K., "Eye tracking in advanced interface design", in W. Barfield and T. Furness (eds.), Advanced interface design and virtual environments, Oxford University Press, Oxford, 1995. In this article, Jacob describes techniques for recognizing fixations and saccades from the raw eye tracker data. Fixation and saccade data alone, however, is still relatively low-level data that is of limited use, and Jacob fails to teach any specific methods for recognizing a user's conscious intentions or mental states. These eye tracking methods, therefore, still fall short of the goal of providing useful information about any higher-level eye behavior or mental states.

One attempt to derive higher-level cognitive information from eye movement data is described by India Starker and Richard A. Bolt in "A gaze-responsive self-disclosing display", CHI '90 Proceedings, April 1990. Their technique correlates eye fixation data with a priori knowledge of objects in the user's field of view (i.e., on the computer screen) to make the inferences about the degree of interest the user has in each object. One major disadvantage of this technique is that it requires a priori knowledge of the objects in the user's visual field, such as their positions, shapes and type information. Consequently, the technique cannot be used in many computer software applications where information about what is displayed on a computer screen is not readily available. In addition, it cannot be used in other situations where a priori knowledge is not available at all, such as when the user is not viewing virtual objects on a computer screen, but physical objects in the real world.

In addition, because the technique disclosed by Starker and Bolt identifies the attention of the user with single fixation points, it fails to accurately distinguish attentively looking at an object from "spacing out" while inattentively gazing at the object. Thus, although the technique attempts to recognize the mental state of attentive interest, it actually fails to properly distinguish this state from non-attentiveness. It will also be noted that Starker and Bolt propose a technique that is limited to identifying just one cognitive state.

Another technique for using eye-movement data is disclosed by Hironobu Takagi in "Development of Predictive CHI with Eye Movements," Master's Thesis, University of Tokyo, Feb. 7, 1996. As stated in the Abstract, Takagi "developed algorithms to extract users' intention and knowledge states from eye-movements" (Takagi, p. 1). Takagi, however, does not disclose any general method for extracting a user's intention from eye movements. Because detailed a priori knowledge of the user task is thought to be required in order to infer user intentions, Takagi only teaches a method that is limited to a very specific task or domain of application. As Takagi states, "Any general methods of analysis derived from known theories cannot be developed. Therefore, we must develop analysis methods for each domain task" (Takagi, pp. 13–14). In other words, Takagi not only fails to teach a general method of extracting a user's intention from eye movement data, he also states that such a general method is impossible using known theories.

Takagi's techniques are also limited by the fact that they require a combination of eye movement data with information about the objects being viewed by the user. In order to extract information about a user's intentions, Takagi measures eye movement data and combines it with a priori knowledge about the contents of the user's field of vision, i.e., the contents of the computer display. Because predetermined regions of the screen are known to contain objects with specific meaning, the eye movement data can be correlated with these regions and interpreted. Two of Takagi's algorithms, for example, assume the screen is divided into rectangular regions termed "columns", then correlates eye movements to these specific columns (Takagi, p. 31–32). Thus, the technique "analyzed data concerning regions that divide stimuli. Eye movements were not transformed into fixation-saccade data. This is a weak point of the method. We cannot transform eye-movements data into fixation-saccade data because of some problems" (Takagi, p. 45). Thus, not only does Takagi require a priori knowledge of the content of specific regions in user's visual field, but Takagi's method only measures the region within which the user is gazing, and does not measure detailed fixation-saccade data. Moreover, Takagi proposes "to analyze long term eye movements statistically" (Takagi, p. 31). These statistical methods are performed "with disregard for details of eye movements" (Takagi, p. 28). Such statistical methods, in other words, ignore the detailed spatiotemporal trajectories of eye movements and consider only statistical features of the movements within coarsely defined regions that must be known a priori by Takagi's system.

Takagi's technique is also limited in other important respects. For example, Takagi's techniques depend on a prior knowledge of the tasks and "only analyze periods when users carry out the main goal of the task" (Takagi, p. 45). Regarding the long-standing problem of correctly relating eye fixations with user attentions, Takagi acknowledges that his technique does "not deal with this problem" (Takagi, p. 28). It is clear, therefore, that the prior art techniques for interpreting eye tracker data suffer from one or more of the following disadvantages: they fail to properly identify user attention or intention, they do not identify a variety of mental states, they are limited to very specific and predetermined user tasks, and they require a priori knowledge of objects in the user's field of vision.

SUMMARY

In view of the above, it is an object of the present invention to overcome the disadvantages and limitations of existing methods for deriving useful information from eye tracker data. In particular, it is an object of the present invention to provide a method for accurately recognizing a variety of high-level mental states of a user from eye tracker data. It is another object of the invention to provide such a technique that does not require a priori information about objects in the user's visual field, and is not limited to situations where the user is looking at a computer screen. Yet another object of the invention is to provide a method for analyzing user mental states from detailed fixation-saccade data rather than from statistical data derived from eye movements. An additional object of the invention is to provide a technique for inferring mental states of a user without requiring a priori knowledge of the task the user is engaged in, or of the contents and locations of specific regions at which the user is looking.

These and other objects and advantages are provided by a computer-implemented method for inferring mental states of a person from eye movements of the person. The method includes identifying elementary features of eye tracker data, such as fixations, saccades, and smooth pursuit motion. Identifying a fixation typically includes identifying a fixation location and a fixation duration. Identifying a saccade typically involves identifying a beginning and end location of the eye-movement, as well as possibly determining the velocity and other characteristics of the movement. It will be noted that for many applications that do not consider the velocity of the saccade, identifying two successive fixations can be used to identify a saccade. Identifying smooth pursuit motion typically includes identifying the velocity and path the eye takes as it smoothly follows a moving object. The method also includes recognizing from the elementary features a plurality of eye-movement patterns, i.e., specific spatiotemporal patterns of fixations, saccades, and/or other elementary features derived from eye tracker data. Each eye-movement pattern is recognized by comparing the elementary features with a predetermined eye-movement pattern template. A given eye-movement pattern is recognized if the features satisfy a set of criteria associated with the template for that eye-movement pattern. The method further includes the step of recognizing from the eye-movement patterns a plurality of eye-behavior patterns corresponding to the mental states of the person.

BRIEF DESCRIPTION OF THE DRAWINGS

FIGS. 2A–2C are graphical illustrations of three eye movement patterns according to the present invention.

DETAILED DESCRIPTION

Figure 1:
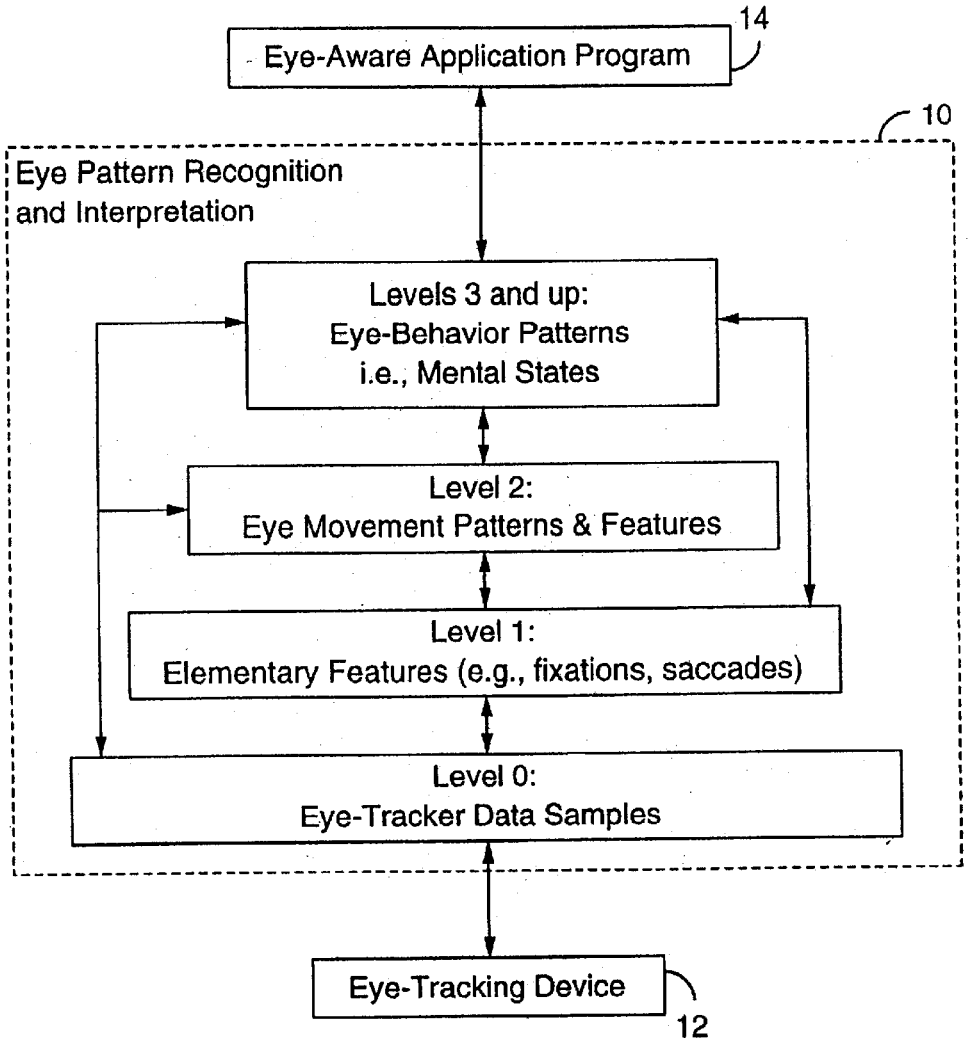
FIG. 1 is a schematic illustration of central components in a preferred embodiment of the present invention and their relationships.

In a preferred embodiment of the present invention, raw data samples representative of eye gaze positions are communicated to a microprocessor 10 from a conventional eye tracking device 12, as illustrated in FIG. 1. Any method for measuring eye position or movement, whether optical, electrical, magnetic, or otherwise, may be used with the present invention. A method of eye pattern recognition and interpretation implemented on the microprocessor processes and analyzes the raw data samples to produce in real time a series of eye behavior patterns which correspond to high level mental states of activities. This generic high-level information is then typically made available to an application program 14 which uses the information to perform application-specific tasks. A few of the many samples of application programs which will benefit from the high level eye pattern information provided by the methods of the present invention are: an on-screen keyboard for the disabled, an eye-controlled pointing device, reading instructional software, an experimental tool in psychological research, an eye-aware web browser, and a user interface for rapid navigation of hierarchical information. The methods of the present invention, however, do not depend on the use of any particular application. In fact, it is a key feature of the present invention that it provides generic, application-independent eye pattern recognition and interpretation. Moreover, the present invention provides for the first time the ability to accurately recognize high-level eye behavior patterns independent of any a priori knowledge of the content of the user's visual field or other contextual information. Provided suitable eye position of data is available, the present invention is even able to recognize eye patterns and mental states of a person who is dreaming or mentally disengaged from the external world in other ways.

In accordance with the teachings of the present invention, eye pattern recognition and interpretation is performed by a collection of hierarchical levels of data interpretation. As illustrated in FIG. 1 and in TABLE I, the fundamental level of data is LEVEL 0, which corresponds to the raw, uninterpreted eye-tracker data samples. The first level of interpretation, LEVEL 1, involves identifying elementary features such as fixations and saccades from the raw data provided by LEVEL 0. It is at this primitive level of interpretation that prior methods end. The present invention, in contrast, provides one or more additional higher-level interpretations of the data. In a preferred embodiment, LEVEL 2 interpretation involves identifying from the fixations and saccades eye-movement patterns, typically consisting of a set of several fixations and/or saccades satisfying certain predetermined criteria. LEVEL 3 interpretation, in turn, involves identifying from the LEVEL 2 eye movement patterns various eye-behavior patterns. These eye-behavior patterns typically consist of various movement patterns satisfying particular criteria. Additional levels may provide higher levels of interpretation that build on previous levels. The highest interpretive levels correspond with mental states of the user. For the purposes of this description, a mental state of the user includes mental activities, mental intentions, mental states, and other forms of cognition, whether conscious or unconscious.

TABLE 1

| Interpretive Level | Description |
|---|---|
| LEVELS 3 and up | EYE-BEHAVIOR PATTERNS <=> MENTAL STATES |
| LEVEL 2 | EYE-MOVEMENT PATTERNS |
| LEVEL 1 | ELEMENTARY FEATURES FIXATIONS/SACCADES |
| LEVEL 0 | EYE-TRACKER DATA SAMPLES |

It will be noted, as indicated in FIG. 1, that higher levels of interpretation can make use of interpretative data on more than one lower level. For example, although LEVEL 3 intepretation is based primarily upon the results of LEVEL 2 intepretation, it may also make use of LEVEL 1 fixation and saccade information, or even LEVEL 0 raw data if necessary. It should also be noted that information in higher levels of the hierarchy can be provided to lower levels for various useful purposes. For example, criteria for recognizing fixations during LEVEL 1 interpretation can be adjusted in dependence upon the current mental state derived from LEVEL 3 interpretation. This feature permits the system to be dynamically and intelligently adaptive to different users as well as to different mental states of a single user.

We now turn to a more detailed discussion of the various levels of interpretation mentioned above. TABLE II below lists the typical information present at LEVEL 0. Commonly available eye tracker devices generate a data stream of 10 to 250 position samples per second. In the case of monocular eye trackers, the z component of the gaze position is not present. Eye trackers are also available that can measure pupil diameter. These pupil measurements provide additional information that can be useful at various levels of interpretation (e.g., pupil constriction during fixation can be used to refine selection). Typical eye tracker devices derive eye position data from images of the eye collected by a CCD camera. Other techniques for deriving eye position data, however, are also possible. For example, eye trackers can infer the position of the eye from physiological measurements of electropotentials on the surface of the skin proximate to the eye. It will be appreciated that these and other techniques for producing a LEVEL 0 data stream of eye information are all compatible with the methods of the present invention. After the LEVEL 0 data stream is collected, it is preferably analyzed in real time by a LEVEL 1 interpretation procedure. The LEVEL 0 data stream may also be stored in a memory buffer for subsequent analysis.

TABLE II

| LEVEL 0: EYE TRACKER DATA SAMPLES |
|---|
| Eye gaze position (x, y, z) |
| Sample time (t) |
| Pupil diameter (d) |
| Eye is opened or closed (percentage) |

The LEVEL 1 interpretation procedure identifies elementary features of the eye data from the LEVEL 0 eye tracker data. As indicated in Table III, these elementary features include fixations and saccades. FIG. 2A is a graphical illustration of a sequence of fixations and saccades, with the fixations represented as solid dots and the saccades represented by directed line segments between the dots. Many techniques are well-known in the art for identifying and recognizing from eye tracker data fixations, saccades, and other elementary features. It will be appreciated that LEVEL 1 interpretation may also identify other elementary features of the LEVEL 0 data, such as smooth pursuit motion. These features are stored in a memory buffer allocated for LEVEL 1 data.

TABLE III

| LEVEL 1: ELEMENTARY FEATURES: (e.g., FIXATIONS and SACCADES) | |
|---|---|
| Elementary Feature | Feature Attributes |
| Fixation | Position, time, duration |
| Saccade | Magnitude, direction, velocity |
| Smooth Pursuit Motion | Path taken by eye, velocity |
| Blinks | Duration |

Identifying a fixation typically involves identifying a fixation location and a fixation duration. In the context of the present description, a fixation is defined as a statistically significant clustering of raw eye tracker data within some space-time interval. For example, a fixation may be identified by analyzing the raw eye tracker data stream to determine if most of the eye positions during a predetermined minimum fixation time interval are within a predetermined fixation space interval. In the case of a current state-of-the art eye tracker, the data stream is analyzed to determine if at least 80% of the eye positions during any 50 ms time interval are contained within any 0.25 degree space interval. Those skilled in the art will appreciate that these particular values may be altered to calibrate the system to a particular eye tracker and to optimize the performance of the system. If the above criteria are satisfied, then a fixation is identified. The position and time of the identified fixation can be selected to be the position and time of a representative data point in the space-time interval, or can be derived from the fixation data in the space-time interval (e.g. by taking the median or mean values). The duration of the identified fixation can then be determined by finding the extent to which the minimum fixation time interval can be increased with while retaining a proportion of the positions within a given space interval. For example, the time interval can be extended forward or backward in time by a small amount, and the data within the extended interval is analyzed to determine if an 80% proportion of the positions in the time interval are within some 1 degree space interval.

It will be appreciated that this particular technique for identifying fixations is just one example of how a fixation might be identified, and then other specific techniques for identifying fixations can be used in the context of the present invention, provided they identify clustering of eye tracker data in space and time that correlates with physiological eye fixations. It will also be appreciated that the specific techniques used for identifying fixations (and other elementary features) will depend on the precision, accuracy, and spatiotemporal resolution of the eye tracker used. In order to reduce the false identification of elementary features, a high performance eye tracker is preferred. An ideal eye tracker will have sufficient precision, accuracy, and resolution to permit identification of physiological fixations with a high degree of confidence. Those skilled in the art will also appreciate that the techniques for recognizing a revisit and other eye movement patterns described herein will depend on the performance of the eye tracker used. The specific techniques described herein are appropriate for average performance eye trackers, which have a spatial resolution of approximately 1 degree.

For many purposes a saccade can be tracked as simply the displacement magnitude and direction between successive fixations, though the changes in velocity do contain information useful for understanding the eye movement more specifically. The saccades may be explicitly identified and entered the LEVEL 1 memory buffer, or may remain implicit in the fixation information stored in the buffer. Conversely, it will be appreciated that saccade information implicitly contains the relatively positions of fixations.

In addition to fixations and saccades, elementary features may include various other features that may be identified from the raw eye tracker data, such as blinks, smooth pursuit motion, and angle of eye rotation within the head. Those skilled in the art will appreciate that various elementary features may be defined and identified at this elementary level, and then used as the basis for higher level interpretation in accordance with the teachings of the present invention. Thus, the use of various other elementary features does not depart from the spirit and scope of the present invention.

The elementary features, such as saccades, fixations, smooth pursuit motion and blinks, now form the basis for further higher level interpretation. This LEVEL 2 interpretation involves recognizing eye-movement patterns. An eye movement pattern is a collection of several elementary features that satisfies a set of criteria associated with a predetermined eye-movement pattern template. As shown in TABLE IV below, various eye-movement patterns can be recognized at this level of interpretation. Typically, in practice, after each saccade the data is examined to check if it satisfies the criteria for each of the movement patterns.

TABLE IV

LEVEL 2: EYE-MOVEMENT PATTERN TEMPLATES

| Pattern | Criteria |
|---|---|
| Revisil | The current fixation is within 1.2 degrees of one of the last five fixations, excluding the fixation immediately prior to the current one |
| Significant Fixation | A fixation of significantly longer duration when compared to other fixations in the same category |
| Vertical Saccade | Saccade Y displacement is more than twice saccade X displacement, and X displacement is less than 1 degree |
| Horizontal Saccade | Saccade X displacement is more than twice saccade Y displacement, and Y displacement is less than 1 degree |
| Short Saccade Run | A sequence of short saccades collectively spanning a distance of greater than 4 degrees |
| Selection Allowed | Fixation is presently contained within a region that is known to be selectable |

If LEVEL 1 data fits one of the LEVEL 2 eye-movement pattern templates, then that pattern is recognized and a pattern match activation value is determined and stored in a LEVEL 2 memory buffer. The pattern match activation value can be an on/off flag, or a percentage value indicating a degree of match. It should be noted that some LEVEL 2 patterns may have criteria based on LEVEL 0 data, or other LEVEL 2 data. Normally, however, LEVEL 2 pattern templates have criteria based primarily on LEVEL 1 information. It should also be noted that the eye-movement patterns are not mutually exclusive, i.e., the same LEVEL 1 data can simultaneously satisfy the criteria for more than one eye-movement pattern template. This "pandemonium model" approach tolerates ambiguities at lower levels of interpretation, and allows higher levels of interpretation to take greater advantage of the all the information present in the lower levels.

In addition to recognizing patterns, LEVEL 2 interpretation also may include the initial computation of various higher level features of the data. These LEVEL 2 features and their attributes are shown in TABLE V below. In the preferred embodiment, the term "short saccade" means a saccade of magnitude less than 3 degrees, while the term "long saccade" means a saccade of magnitude at least 3 degrees. It will be appreciated, however, that this precise value is an adjustable parameter.

TABLE V

LEVEL 2: EYE-MOVEMENT FEATURES

| Feature | Attributes |
|---|---|
| Saccade Count | Number of saccades since the last significant fixation or last identification of higher level pattern |
| Large Saccade Count | Number of large saccades since the last significant fixation or last identification of higher level pattern |

These features are used in the interpretation process in LEVEL 2 and higher levels. The movement patterns recognized on LEVEL 2 are also used to recognize other movement patterns, as well as behavior patterns on higher levels. For example, revisits can be used to determine when a user has found a target after searching. Significant fixations, i.e., fixations whose duration are abnormally long, tend to convey information about the change in user state. Examining the length of sequences of saccade can provide information regarding the mental activity of the user. For example, consider the fact that a person can clearly perceive the area around a spot where a significant fixation occurred. Thus, if the user makes a small saccade from that spot, then the user is making a knowledgeable movement because he is moving into an area visible through peripheral vision. If the user makes a short saccade run, as illustrated in FIG. 2A, the user is looking for an object locally. If, on the other hand, the user makes a large saccade after a significant fixation, followed by one or two small saccades, as illustrated in FIG. 2C, then this represents knowledge movement to a remembered location. This pattern of moving with knowledge is normally considered to hold until a different pattern is identified from further data. For example, multiple saccades, illustrated in FIG. 2B, can indicate a pattern of global searching, which normally happens when the user is searching a large area for a target.

During searching, a fixation that is a revisit is treated as being in the knowledgeable movement category as long as that fixation lasts. This covers the situation when a user is searching, briefly perceives the desired target, moves to a new location before realizing that he just passed the desired target, and then moves back to (i.e., revisits) the previous fixation. Recognizing revisits makes it possible to transition back to knowledgeable movement after a user has been searching. It is relatively easy to recognize when a user has begun searching. This technique makes it possible to make the more difficult recognition of when the user has stopped searching.

The eye movement patterns and features of LEVEL 2 form the basis for recognizing higher level eye behavior patterns during the LEVEL 3 interpretation. An eye behavior pattern is a collection of several eye movement patterns that satisfies a set of criteria associated with a predetermined eye-behavior pattern technique. TABLE VI lists examples of common eye-behavior patterns. As with the previous level, these patterns are not necessarily mutually exclusive, allowing yet higher levels of interpretation, or an application program, to resolve any ambiguities. It will be appreciated that many other behavior patterns may be defined in addition to those listed in TABLE VI below.

It should be emphasized that, with the exception of recognizing an "intention to select," the recognition of eye behavior patterns and eye movement patterns do not make explicit or implicit reference to any details regarding the contents of the user's visual field. Thus the present invention provides a technique for recognizing mental states of a user without requiring any a priori knowledge of the contents of the user's visual field. For the purpose of this description, knowledge of the contents of a visual field is understood to mean information regarding one or more objects that are known (1) to be displayed in the visual field and (2) to have specific locations in the visual field or to have specific relative or absolute spatial structuring or layout in the visual field. For example, knowledge that a text box is displayed to the user at a specific location on a computer screen is knowledge of the contents of the user's visual field. In contrast, general knowledge regarding the type of activity of the user, or the types of objects that potentially might appear to the user, are not considered knowledge of contents in the visual field. Thus, for example, if it is known that a user is looking at a computer while browsing the web, that is not considered knowledge of the contents of a user's visual field. If additional knowledge were available, such as knowledge of any specific object on the screen and the object's specific location or spatial relationship with another object, or other such information about specific content, then this would constitute knowledge of contents in the visual field. In addition, it should be emphasized that generic knowledge of the types of objects viewed by the user is also not considered knowledge of content in the visual field unless that knowledge includes specific objects having specific locations and/or spatial relationships with other objects.

TABLE VI

LEVELS 3 and up: EYE-BEHAVIOR PATTERN TEMPLATES

| Pattern | Criteria |
|---|---|
| Best Fit Line (to the Left or Right) | A sequence of at least two horizontal saccades to the left or right. |
| Reading | Best Fit Line to Right or Short Horizontal Saccade while current state is reading |
| Reading a Block | A sequence of best fit lines to the right separated by large saccades to the left, where the best fit lines are regularly spaced in a downward sequence and (typically) have similar lengths |
| Re-Reading | Reading in a previously read area |
| Scanning or Skimming | A sequence of best fit lines to the right joined by large saccades with a downward component, where the best fit lines are not regularly spaced or of equal length |
| Thinking | several long fixations, separated by short spurts of saccades |
| Spacing Out | several long fixations, separated by short spurts of saccades, continuing over a long period of time |
| Searching | A Short Saccade Run, Multiple Large Saccades, or many saccades since the last Significant Fixation or change in user state |
| Re-acquaintance | Like searching, but with longer fixations and consistent rhythm |
| Intention to Select | "selection allowed" flag is active and searching is active and current fixation is significant |

Figure 3A:
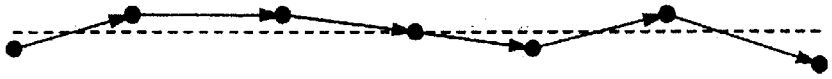
FIGS. 3A–3D are graphical illustrations of four higher level eye behavior patterns according to the present invention.
Figure 3B:
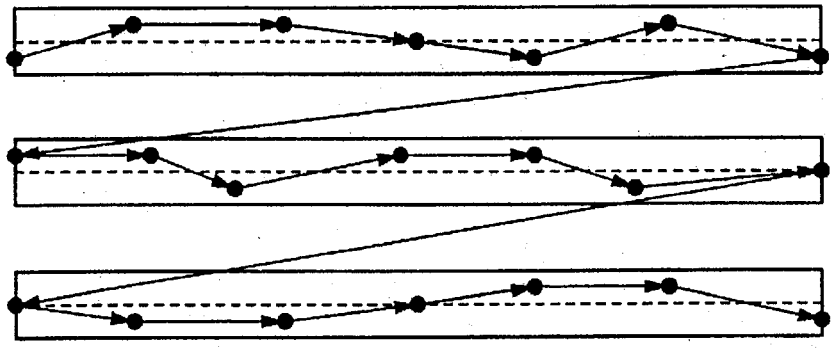
Figure 3C:
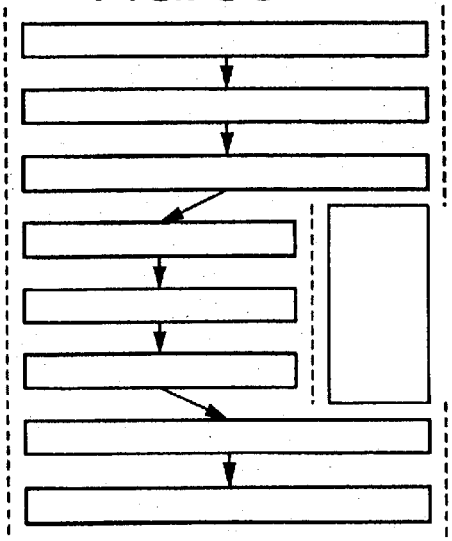
Figure 3D:
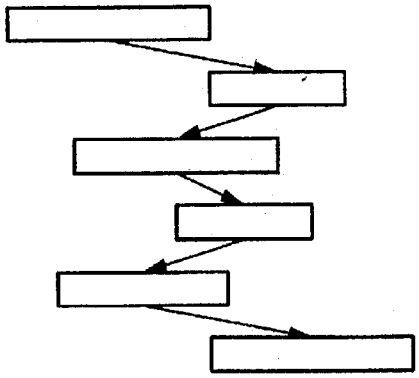

FIG. 3A illustrates an example of a sequence of several horizontal short saccades to the right, a pattern that would be recognized as reading a line of text. A best fit line through the sequence is indicated in the figure by a dashed line. FIG. 3B illustrates an example of how the reading a line of text pattern may be used as a basis for recognizing a higher level pattern. In this case, a sequence of three best fit lines to the right are joined by large saccades to the left. The best fit lines are regularly spaced in a downward sequence and have similar lengths, reflecting the margins of the test. This higher level pattern represents reading a block of text. FIG. 3C illustrates how keeping track of the right and left margins (indicated by dashed vertical lines) while reading lines of text (indicated by rectangles) can be used to recognize when the text flows around a picture or other graphical object. FIG. 3D illustrates a high level pattern corresponding to scanning or skimming a page of text.

These examples illustrate how higher level cognitive patterns can be recognized from lower level eye movement patterns. It should also be noted that some LEVEL 3 behavior patterns are more introverted (e.g., spacing out) while others are more extroverted (e.g., reading or searching). Therefore, a mental introversion pattern can be recognized by testing for a shift from more extroverted behavior patterns to more introverted behavior patterns. Other cognitive patterns can similarly be defined and recognized. For example, the level of knowledge of the user can be determined by observing the number of transitions between behaviors in a given time period. There is no theoretical limit to the number of patterns or interpretive levels that may be introduced and implemented in accordance with the principles of the present invention.

It should be understood that the distinctions between the interpretive levels may be redefined or moved in various ways without altering the nature of the invention. In particular, patterns on one level may be considered to reside on another level than has been shown above. For example, searching may be considered to be a LEVEL 4 behavior pattern rather than a LEVEL 3 movement pattern. Even when such changes are made, however, the hierarchical structure of levels of the interpretation process, and the way in which a collection of recognized patterns on one level are used as the basis for recognizing patterns on a higher level remains unchanged.

It will be appreciated that because implementation of the present method on the hardware level is necessarily linear, the hierarchical nature of the pattern interpretation will be manifested as a repetition of various low-level interpretive processing steps which are used in higher-level recognition. Regardless of whether this repetition takes the form of a single set of instructions repeatedly executed or a series of similar instructions executed in sequence, the hierarchical interpretation technique is nevertheless present.

While the present invention enjoys the advantage that it provides high level recognition of mental states based on eye data alone, if contextual data is available (e.g., specific information about the positions of objects on a computer screen, or general knowledge of what type of information is in the user's field of view) it can be used to supplement the eye data and improve performance. For example, if it is known that text is being displayed in a specific region of the screen, then this information can be used to more accurately determine from the eye data what behavior a user is engaged in while looking within that region. In addition, if it is known that a certain region is selectable, then this contextual information can be provided to the system to allow recognition of the behavior of intending to select a selectable item, as indicated by the "selection allowed" behavior pattern in TABLE IV.

The present invention also enjoys the advantage that high level behaviors can be used to assist in providing a behavioral context in recognizing lower level patterns. For example, significant fixations are recognized using criteria that are automatically updated and selected according to current behavior. The user's fixation duration times are recorded and classified by type of behavior (e.g., searching, reading, looking at a picture, thinking, or knowledgeable movement). Typically, for a given behavior that allows selection, the distribution of fixations with respect to duration time has a first peak near a natural fixation duration value, and a second peak near a fixation duration value corresponding to fixations made with an intention to select. The significant fixation threshold is selected for a given behavior by choosing a threshold between these two peaks. The threshold values for the behaviors are updated on a regular basis and used to dynamically and adaptively adjust the significant fixation thresholds. For example, if a user's familiarity with the locations of selectable targets increases, the natural fixation times will decrease, causing the significant fixation threshold to be automatically set to a lower level. This automatic adaptation allows the user to more quickly make accurate selections. Alternatively, a user may wish to manually fix a specific set of threshold values for the duration of a session.

It should be noted that a user who is unfamiliar with the contents of a visual field will typically display lots of searching activity, while a user who is very familiar with the contents of a visual field will typically display lots of knowledgeable looking. Thus, a user's familiarity with the contents of the visual field can be estimated by measuring the ratio of the frequency of intentional fixations to the frequency of natural fixations.

The present invention has the highly advantageous feature tat it overcomes the long-standing "Midas Touch" problem relating to selecting items on a computer screen using eye-tracking information. Because the technique provided by the present invention identifies various high level mental states, and adaptively adjusts significant fixation thresholds depending on specific attributes of fixation in the current mental state, false selections are not accidentally made with the person is not engaged in selection activities. For example, while currently recognizing a searching behavior, the system will tolerate longer fixations without selection than while recognizing knowledgeable movement. In short, the key to solving the Midas Touch problem is to adaptively adjust target selection criteria to the current mental state of the user. Because prior art techniques were not able to recognize various high level mental states, however, they had no basis for meaningfully adjusting selection criteria. Consequently, false selections were inevitably made in various behavioral contexts due to the use of inappropriate target selection criteria.

What is claimed is:

1. A computer implemented method for inferring mental states of a person from eye movements of the person in real time, the method comprising:

a) identifying a plurality of elementary features of eye tracker data for the person;

b) computing from the elementary features of a plurality of eye movement patterns, wherein each pattern satisfies a set of predetermined eye movement pattern template criteria, wherein computing eye movement patterns is performed without requiring any a priori knowledge of contents of the person's visual field; and c) computing from the eye movement patterns a plurality of eye-behavior patterns corresponding to mental states of the person.

2. The method of claim 1 further comprising classifying the elementary features according to associated eye-behavior patterns.

3. The method of claim 2 wherein computing the eye movement patterns comprises computing a significant fixation when a current fixation duration is longer than a significant threshold for a current eye-behavior, where the threshold is calculated from recent fixation duration times classified by the current eye-behavior.

4. The method of claim 1 further comprising computing high level features from the elementary features.

5. The method of claim 1 wherein the plurality of eye behavior patterns comprises at least three eye behavior patterns.

6. The method of claim 5 wherein the eye behavior patterns comprise a pattern selected from the group consisting of reading patterns, spacing out patterns, and searching patterns.

7. The method of claim 1 wherein computing eye movement patterns is performed without requiring knowledge of specific types of objects being displayed in the person's visual field.

8. The method of claim 1 being documented in a machine-readable code and being stored on a computer storage device.

9. A computer implemented method for inferring mental states of a person from eye movements of the person in real time, the method comprising:

a) identifying a plurality of elementary features of eye tracker data for the person;

b) computing from the elementary features of a plurality of eye movement patterns, wherein each pattern comprises a temporally ordered sequence of fixations and saccades satisfying a set of predetermined eye movement pattern template criteria; and c) computing from the eye movement patterns a plurality of eye-behavior patterns corresponding to mental states of the person.

10. The method of claim 9 further comprising classifying the elementary features according to associated eye-behavior patterns.

11. The method of claim 10 wherein computing the eye movement patterns comprises computing a significant fixation when a current fixation duration is longer than a significant fixation threshold for a current eye-behavior, where the threshold is calculated from recent fixation duration times classified by the current eye-behavior.

12. The method of claim 9 further comprising computing high level features from the elementary features.

13. The method of claim 9 wherein the plurality of eye behavior patterns comprises at least three eye behavior patterns.

14. The method of claim 13 wherein the eye behavior patterns comprise a pattern selected from the group consisting of reading patterns, spacing out patterns, and searching patterns.

15. The method of claim 9 wherein computing the eye behavior pattern comprises identifying a sequence of short saccades to the right.

16. The method of claim 9 being documented in a machine-readable code and being stored on a computer storage device.

17. A computer implemented method for inferring from eye movements of a person that the person is reading, the method comprising:

a) identifying elementary features of eye tracker data for the person;

b) computing from the elementary features a hierarchy of patterns on various interpretive levels, wherein computed patterns on higher levels are derived from computed patterns on lower levels, wherein highest level computed patterns comprise a reading corresponding to a reading state of the person.

18. The method of claim 17 wherein computing patterns on various interpretive levels comprises identifying a sequence of short saccades to the right.

19. The method of claim 17 wherein computing patterns on various interpretive levels comprises identifying a plurality of sequences of short saccades to the right, wherein the plurality of sequences are approximately vertically aligned with each other.

20. The method of claim 17 wherein computing patterns on various interpretive levels and computing highest level patterns is accomplished without requiring any a priori knowledge of the person's visual field.

21. The method of claim 17 being documented in a machine-readable code and being stored on a computer storage device.

*22. An article storing computer-readable instructions that cause one or more hardware devices to:*

*a) identify a plurality of elementary features of eye tracker data for the person;*

*b) compute from the elementary features a plurality of eye movement patterns, wherein each pattern satisfies a set of predetermined eye movement pattern template criteria, wherein computing eye movement patterns is performed without requiring any a priori knowledge of contents of the person's visual field; and*

*c) compute from the eye movement patterns a plurality of eye-behavior patterns corresponding to mental states of the person.*

*23. The article of claim 22 further comprising instructions to classify the elementary features according to associated eye-behavior patterns.*

*24. The method of claim 23 wherein the instructions to compute the eye movement patterns comprises instructions to compute a significant fixation when a current fixation duration is longer than a significant threshold for a current eye-behavior, where the threshold is calculated from recent fixation duration times classified by the current eye-behavior.*

*25. The article of claim 22 further comprising instructions to compute high level features from the elementary features.*

*26. The article of claim 22 wherein the plurality of eye behavior patterns comprises at least three eye behavior patterns.*

*27. The article of claim 26 wherein the eye behavior patterns comprise a pattern selected from the group consisting of reading patterns, spacing out patterns, and searching patterns.*

*28. The article of claim 22 wherein computing eye movement patterns is performed without requiring knowledge of specific types of objects being displayed in the person's visual field.*

*29. An article storing computer-readable instructions that cause one or more hardware devices to:*

*a) identify a plurality of elementary features of eye tracker data for the person;*

*b) compute from the elementary features a plurality of eye movement patterns, wherein each pattern comprises a temporally ordered sequence of fixations and saccades satisfying a set of predetermined eye movement pattern template criteria; and*

*c) compute from the eye movement patterns a plurality of eye-behavior patterns corresponding to mental states of the person.*

*30. The article of claim 29 further comprising instructions to classify the elementary features according to associated eye-behavior patterns.*

*31. The article of claim 30 wherein computing the eye movement patterns comprises computing a significant fixation when a current fixation duration is longer than a significant fixation threshold for a current eye-behavior, where the threshold is calculated from recent fixation duration times classified by the current eye-behavior.*

*32. The article of claim 29 further comprising computing high level features from the elementary features.*

*33. The article of claim 29 wherein the plurality of eye behavior patterns comprises at least three eye behavior patterns.*

*34. The article of claim 33 wherein the eye behavior patterns comprise a pattern selected from the group consisting of reading patterns, spacing out patterns, and searching patterns.*

*35. The article of claim 29 wherein computing the eye behavior patterns comprises identifying a sequence of short saccades to the right.*

*36. An article storing computer-readable instructions that cause one or more hardware devices to:*

*a) identifying elementary features of eye tracker data for the person;*

*b) compute from the elementary features a hierarchy of patterns on various interpretive levels, wherein computed patterns on higher levels are derived from computed patterns on lower levels, wherein highest level computed patterns comprise a reading pattern corresponding to a reading state of the person.*

*37. The article of claim 36 wherein computing patterns on various interpretive levels comprises identifying a sequence of short saccades to the right.*

*38. The article of claim 36 wherein computing patterns on various interpretive levels comprises identifying a plurality of sequences of short saccades to the right, wherein the plurality of sequences are approximately vertically aligned with each other.*

*39. The article of claim 36 wherein computing patterns on various interpretive levels and computing highest level patterns is accomplished without requiring any a priori knowledge of the person's visual field.*

* * * * *